US012708520B2

(12) United States Patent
Emstad et al.

(10) Patent No.: US 12,708,520 B2
(45) Date of Patent: Aug. 18, 2026

(54) EXPANDABLE INTERVERTEBRAL IMPLANT

(71) Applicant: Elevation Spine, Inc., Monterey, CA (US)

(72) Inventors: Erik Emstad, Laurel Springs, NC (US); Andrea Cragen, Austin, TX (US); Charles Gilbride, Salinas, CA (US); Martin Klazmer, Memphis, TN (US)

(73) Assignee: Elevation Spine, Inc., Monterey, CA (US)

( * ) Notice: Subject to any disclaimer, the term of this patent is extended or adjusted under 35 U.S.C. 154(b) by 61 days.

(21) Appl. No.: 18/822,403

(22) Filed: Sep. 2, 2024

(65) Prior Publication Data

US 2025/0107902 A1 Apr. 3, 2025

Related U.S. Application Data

(60) Provisional application No. 63/541,798, filed on Sep. 30, 2023.

(51) Int. Cl.
*A61F 2/44* (2006.01)
*A61F 2/30* (2006.01)

(52) U.S. Cl.
CPC .. *A61F 2/4425* (2013.01); *A61F 2002/30518* (2013.01)

(58) Field of Classification Search
CPC .......... A61F 2/44; A61F 2/442; A61F 2/4425; A61F 2/4455; A61F 2/446; A61F 2/4465; A61F 2/447; A61F 2002/443
See application file for complete search history.

(56) References Cited

U.S. PATENT DOCUMENTS

| | | | |
|---|---|---|---|
| 5,171,278 | A | 12/1992 | Pisharodi |
| 5,653,763 | A | 8/1997 | Errico et al. |
| 5,665,122 | A | 9/1997 | Kambin |
| 5,693,100 | A | 12/1997 | Pisharodi |
| 6,129,763 | A | 10/2000 | Chauvin et al. |
| 6,159,244 | A | 12/2000 | Suddaby |
| 6,174,334 | B1 | 1/2001 | Suddaby |
| 6,193,757 | B1 | 2/2001 | Foley et al. |
| 6,436,140 | B1 | 8/2002 | Liu et al. |
| 6,641,614 | B1 | 11/2003 | Wagner et al. |
| 6,723,126 | B1 | 4/2004 | Berry |
| 6,905,512 | B2 | 6/2005 | Paes et al. |

(Continued)

FOREIGN PATENT DOCUMENTS

| | | | |
|---|---|---|---|
| CN | 201861800 | U | 6/2011 |
| EP | 2677969 | B1 | 8/2017 |

(Continued)

*Primary Examiner* — Ellen C Hammond
(74) *Attorney, Agent, or Firm* — Schwegman, Lundberg & Woessner, P.A.

(57) ABSTRACT

In some embodiments, an expandable intervertebral implant may include a superior plate configured to engage a superior vertebra, an inferior plate configured to engage an inferior vertebra, wherein the inferior plate is spaced apart from the superior plate by a gap, one or more first sliders moveable along a first direction to urge linear expansion of the gap, and one or more second sliders moveable along a second direction, nonparallel to the first direction, to urge angular expansion of the gap.

15 Claims, 13 Drawing Sheets

(56) References Cited

U.S. PATENT DOCUMENTS 7,094,257 B2 8/2006 Mujwid et al.
7,410,501 B2 8/2008 Michelson
7,569,074 B2 8/2009 Eisermann et al.
7,655,043 B2 2/2010 Peterman et al.
7,655,046 B2 2/2010 Dryer et al.
7,674,296 B2 3/2010 Rhoda et al.
7,749,270 B2 7/2010 Peterman
7,753,958 B2 7/2010 Gordon et al.
7,819,921 B2 * 10/2010 Grotz .................... A61F 2/4611 606/90
7,951,180 B2 5/2011 Moskowitz et al.
7,967,867 B2 6/2011 Barreiro et al.
7,985,256 B2 7/2011 Grotz et al.
8,062,375 B2 11/2011 Glerum et al.
8,110,004 B2 2/2012 Valdevit et al.
8,118,870 B2 2/2012 Gordon et al.
8,192,495 B2 6/2012 Simpson et al.
8,221,502 B2 7/2012 Branch, Jr. et al.
8,303,663 B2 11/2012 Jimenez et al.
8,353,963 B2 1/2013 Glerum
8,357,181 B2 1/2013 Lange et al.
8,366,777 B2 2/2013 Matthis et al.
8,377,133 B2 2/2013 Yuan et al.
8,394,143 B2 3/2013 Grotz et al.
8,398,713 B2 3/2013 Weiman
8,409,286 B2 4/2013 McKay
8,480,741 B2 7/2013 Grotz
8,486,149 B2 7/2013 Saidha
8,523,944 B2 9/2013 Jimenez
8,551,173 B2 10/2013 Lechmann
8,574,300 B2 11/2013 McManus
8,628,576 B2 1/2014 Triplett
8,663,329 B2 * 3/2014 Ernst ....................... A61F 2/442 623/17.15
8,679,183 B2 3/2014 Glerum
8,685,098 B2 4/2014 Glerum
8,696,751 B2 4/2014 Ashley
8,702,798 B2 4/2014 Matthis
8,845,731 B2 9/2014 Weiman
8,845,734 B2 9/2014 Weiman
8,852,243 B2 10/2014 Morgenstern Lopez
8,852,279 B2 10/2014 Weiman
8,894,710 B2 11/2014 Simpson
8,894,712 B2 11/2014 Varela
8,926,704 B2 1/2015 Glerum
8,936,641 B2 1/2015 Cain
8,940,052 B2 * 1/2015 Lechmann ............ A61F 2/4425 623/17.11
8,986,387 B1 3/2015 To
8,992,620 B2 3/2015 Ashley
9,066,813 B2 6/2015 Farris
9,119,726 B2 9/2015 Wei
9,125,757 B2 9/2015 Weiman
9,198,772 B2 12/2015 Weiman
9,204,972 B2 12/2015 Weiman
9,271,777 B2 3/2016 Nichols
9,351,848 B2 5/2016 Glerum
9,358,125 B2 6/2016 Jimenez
9,433,510 B2 9/2016 Lechmann
9,474,626 B2 10/2016 Jimenez
9,486,328 B2 11/2016 Jimenez
9,492,288 B2 11/2016 Wagner
9,510,955 B2 12/2016 Marino
9,532,883 B2 1/2017 McLuen
9,539,106 B2 1/2017 Boehm
9,539,108 B2 1/2017 Glerum
9,549,824 B2 1/2017 McAfee
9,554,918 B2 1/2017 Weiman
9,561,117 B2 2/2017 Lechmann
9,572,678 B2 2/2017 Nichols
9,585,766 B2 3/2017 Robinson
9,603,717 B2 3/2017 Ibarra
9,662,223 B2 5/2017 Matthis
9,713,536 B2 7/2017 Foley
9,724,204 B2 8/2017 Hansell
9,750,618 B1 9/2017 Daffinson
9,770,343 B2 9/2017 Weiman
9,782,265 B2 10/2017 Weiman
9,820,865 B2 11/2017 Sharabani
9,839,527 B2 12/2017 Robinson
9,855,151 B2 1/2018 Weiman
9,889,019 B2 2/2018 Rogers
9,907,673 B2 3/2018 Weiman
9,913,727 B2 3/2018 Thommen
9,974,662 B2 5/2018 Hessler
9,974,664 B2 5/2018 Emerick et al.
9,980,823 B2 5/2018 Matthis
9,987,143 B2 6/2018 Robinson
9,987,146 B1 6/2018 Lentner
10,004,607 B2 6/2018 Weiman
10,022,239 B1 7/2018 Lentner
10,034,767 B2 7/2018 Baynham
10,052,215 B2 8/2018 Hessler
10,085,849 B2 10/2018 Weiman
10,098,757 B2 10/2018 Logan
10,098,758 B2 10/2018 Matthews
10,117,755 B2 11/2018 Emerick
10,137,001 B2 11/2018 Weiman
10,159,583 B2 12/2018 Dietzel
10,182,922 B2 1/2019 Nichols
10,219,914 B2 3/2019 Faulhaber
10,285,824 B2 5/2019 Robinson
10,299,935 B2 5/2019 Loebl
10,322,009 B2 6/2019 Aghayev
10,350,081 B2 7/2019 Seifert
10,363,142 B2 7/2019 McClintock
10,383,741 B2 8/2019 Butler
10,390,962 B2 8/2019 Weiman
10,398,563 B2 9/2019 Engstrom
10,420,654 B2 9/2019 Logan
10,426,634 B1 10/2019 Al-Jazaeri
10,492,923 B2 12/2019 Zur
10,500,059 B2 12/2019 Grotz
10,507,116 B2 12/2019 Shoshtaev
10,512,550 B2 12/2019 Bechtel et al.
10,524,927 B2 1/2020 Ryan
10,561,502 B2 2/2020 Bernard et al.
10,653,531 B2 5/2020 Werner
10,682,239 B2 6/2020 Hsu
10,682,241 B2 6/2020 Glerum
10,702,392 B2 7/2020 Greenhalgh
10,709,571 B2 7/2020 Iott
10,709,573 B2 7/2020 Weiman
10,722,377 B2 7/2020 Glerum
10,722,379 B2 7/2020 McLaughlin
10,758,367 B2 9/2020 Weiman
10,779,957 B2 9/2020 Weiman
10,806,596 B2 10/2020 Iott
10,835,387 B2 11/2020 Weiman
10,842,644 B2 11/2020 Weiman
10,856,997 B2 12/2020 Cowan
10,869,768 B2 12/2020 Weiman
10,869,769 B2 12/2020 Eisen
10,881,524 B2 1/2021 Eisen
10,881,531 B2 1/2021 Berry
10,898,344 B2 1/2021 Alheidt
10,925,752 B2 2/2021 Weiman
10,945,857 B2 3/2021 Emstad
10,945,858 B2 3/2021 Bechtel
10,973,649 B2 4/2021 Weiman
10,980,642 B2 4/2021 Glerum
10,980,644 B2 4/2021 Purcell
11,020,238 B2 6/2021 Nichols
11,026,800 B2 6/2021 Seifert
11,033,401 B2 6/2021 Shoshtaev
11,033,403 B2 6/2021 Predick
11,090,167 B2 8/2021 Emerick
11,103,366 B2 8/2021 Glerum
11,166,826 B2 11/2021 Huang
11,185,421 B1 11/2021 Miller
11,191,650 B2 12/2021 Weiman
11,207,192 B2 12/2021 Suddaby
11,253,372 B2 2/2022 Grotz
11,285,014 B1 3/2022 Josse

(56) References Cited

U.S. PATENT DOCUMENTS 11,285,018 B2 3/2022 Shoshtaev
11,291,554 B1 4/2022 Prevost
11,304,817 B2 4/2022 Altarac
11,304,821 B2 4/2022 Berry
11,337,825 B2 5/2022 Predick
11,344,424 B2 5/2022 Luu
11,344,430 B2 5/2022 Glerum
11,376,134 B1 7/2022 Dewey
11,382,764 B2 7/2022 Predick
11,395,743 B1 7/2022 Hynes
11,446,156 B2 9/2022 Hunziker
11,446,161 B2 9/2022 Rogers
11,446,162 B2 9/2022 Weiman
11,452,614 B2 9/2022 Rogers
11,471,301 B2 10/2022 Jimenez
11,491,025 B2 11/2022 Gilbride
11,517,443 B2 12/2022 Dewey
11,564,724 B2 1/2023 Josse
11,564,807 B2 1/2023 Iott
11,612,499 B2 3/2023 Barfield
11,660,205 B2 5/2023 Rogers
11,717,419 B2 8/2023 Altarac
11,730,608 B2 8/2023 Protopsaltis
11,759,334 B2 9/2023 Klausman
11,793,651 B2 * 10/2023 Berry .................... A61F 2/442
2002/0151977 A1 10/2002 Paes
2002/0161444 A1 10/2002 Choi
2003/0135279 A1 7/2003 Michelson
2004/0088054 A1 5/2004 Berry
2004/0153156 A1 8/2004 Cohen
2004/0162618 A1 8/2004 Mujwid
2005/0010295 A1 1/2005 Michelson
2005/0131536 A1 6/2005 Eisermann
2005/0209698 A1 9/2005 Gordon
2005/0256576 A1 11/2005 Moskowitz
2005/0273174 A1 12/2005 Gordon
2006/0009770 A1 1/2006 Speirs
2006/0129244 A1 6/2006 Ensign
2006/0149385 A1 7/2006 McKay
2006/0206207 A1 9/2006 Dryer
2006/0241770 A1 10/2006 Rhoda
2007/0093901 A1 4/2007 Grotz
2007/0100340 A1 5/2007 Lange
2008/0147194 A1 6/2008 Grotz
2008/0300598 A1 12/2008 Barreiro
2009/0210062 A1 8/2009 Thalgott
2009/0222100 A1 9/2009 Cipoletti
2010/0049324 A1 2/2010 Valdevit
2010/0082109 A1 4/2010 Greenhalgh
2010/0145456 A1 6/2010 Simpson
2010/0168429 A1 7/2010 Halland
2010/0185291 A1 7/2010 Jimenez
2010/0280619 A1 11/2010 Yuan
2010/0286783 A1 11/2010 Lechmann
2011/0015747 A1 1/2011 McManus
2011/0035011 A1 2/2011 Cain
2011/0093074 A1 4/2011 Glerum
2011/0130835 A1 6/2011 Ashley
2011/0160861 A1 6/2011 Jimenez
2011/0172716 A1 7/2011 Glerum
2011/0319997 A1 12/2011 Glerum
2012/0059473 A1 3/2012 Weiman
2012/0116518 A1 5/2012 Grotz
2012/0215313 A1 8/2012 Saidha
2012/0245695 A1 9/2012 Simpson
2012/0265309 A1 10/2012 Glerum
2012/0310350 A1 12/2012 Farris
2012/0323327 A1 12/2012 McAfee
2013/0053966 A1 2/2013 Jimenez
2013/0158663 A1 * 6/2013 Miller .................. A61F 2/4455 623/17.16
2013/0158668 A1 6/2013 Nichols
2013/0197642 A1 8/2013 Ernst
2013/0211525 A1 8/2013 McLuen
2013/0253650 A1 9/2013 Ashley
2013/0274883 A1 10/2013 McLuen
2014/0031938 A1 1/2014 Lechmann
2014/0039622 A1 2/2014 Glerum
2014/0058519 A1 2/2014 Glerum
2014/0094917 A1 4/2014 Salerni
2014/0100660 A1 4/2014 Morgenstern Lopez
2014/0114420 A1 4/2014 Robinson
2014/0148904 A1 5/2014 Robinson
2014/0236296 A1 8/2014 Wagner
2014/0236297 A1 8/2014 Iott
2014/0249628 A1 9/2014 Weiman
2014/0249631 A1 9/2014 Weiman
2014/0249632 A1 9/2014 Weiman
2014/0277474 A1 9/2014 Robinson
2014/0277492 A1 9/2014 Wei
2014/0277500 A1 9/2014 Logan
2014/0288652 A1 9/2014 Boehm
2014/0296984 A1 10/2014 Etminan
2014/0316522 A1 10/2014 Weiman
2015/0012097 A1 1/2015 Ibarra
2015/0012101 A1 1/2015 Glerum
2015/0018957 A1 1/2015 Nichols
2015/0066145 A1 3/2015 Rogers
2015/0073552 A1 3/2015 To
2015/0073555 A1 * 3/2015 To .......................... A61F 2/442 623/17.16
2015/0088258 A1 3/2015 Jimenez
2015/0094813 A1 4/2015 Lechmann
2015/0094814 A1 4/2015 Emerick
2015/0148908 A1 5/2015 Marino
2015/0257892 A1 9/2015 Lechmann
2015/0272743 A1 10/2015 Jimenez
2015/0272746 A1 10/2015 Jimenez
2015/0328012 A1 11/2015 Hansell
2015/0351925 A1 12/2015 Emerick et al.
2015/0366675 A1 12/2015 Matthews
2016/0095718 A1 4/2016 Burkhardt
2016/0106551 A1 4/2016 Grimberg, Jr.
2016/0151168 A1 6/2016 Weiman
2016/0166396 A1 6/2016 McClintock
2016/0242927 A1 8/2016 Seifert et al.
2016/0250034 A1 9/2016 Loebl
2017/0000622 A1 1/2017 Thommen
2017/0035577 A1 2/2017 Iott
2017/0042695 A1 2/2017 Foley
2017/0079807 A1 * 3/2017 Wallenstein ............. A61F 2/44
2017/0119542 A1 5/2017 Logan
2017/0128226 A1 5/2017 Faulhaber
2017/0156884 A1 6/2017 Rathbun
2017/0156885 A1 6/2017 Zur
2017/0172760 A1 6/2017 Loebl
2017/0209282 A1 7/2017 Aghayev
2017/0216046 A1 8/2017 Greenhalgh
2017/0224505 A1 8/2017 Butler
2017/0333198 A1 11/2017 Robinson
2017/0354512 A1 12/2017 Weiman
2018/0000609 A1 1/2018 Hessler
2018/0177603 A1 6/2018 Weiman
2018/0177604 A1 6/2018 Weiman
2018/0185163 A1 7/2018 Weiman
2018/0193164 A1 7/2018 Shoshtaev
2018/0360616 A1 12/2018 Luu
2018/0368983 A1 12/2018 Werner
2019/0021873 A1 1/2019 Dmuschewsky
2019/0070015 A1 3/2019 Emerick
2019/0117409 A1 4/2019 Shoshtaev
2019/0254836 A1 8/2019 Cowan
2019/0269521 A1 9/2019 Shoshtaev
2019/0274836 A1 9/2019 Eisen
2019/0274837 A1 9/2019 Eisen
2019/0298540 A1 10/2019 Aghayev
2019/0307577 A1 10/2019 Predick
2019/0321190 A1 10/2019 Wagner
2019/0321198 A1 10/2019 Glerum
2019/0336302 A1 11/2019 Seifert
2019/0388232 A1 12/2019 Purcell
2020/0078190 A1 3/2020 Rogers
2020/0129307 A1 4/2020 Hunziker
2020/0163775 A1 5/2020 Kim

(56) References Cited

U.S. PATENT DOCUMENTS

2020/0281741 A1 9/2020 Grotz
2020/0315811 A1 10/2020 Cryder
2020/0352731 A1 11/2020 Berry
2020/0352738 A1 11/2020 Berry
2020/0390565 A1 12/2020 Jimenez
2021/0000160 A1 1/2021 Olmos
2021/0045891 A1 2/2021 Rogers
2021/0045892 A1 2/2021 Rogers
2021/0121300 A1 4/2021 Weiman
2021/0137695 A1 5/2021 Huang
2021/0186706 A1 6/2021 Spitler
2021/0236298 A1 8/2021 Weiman
2021/0251770 A1 8/2021 Purcell
2021/0322179 A1 10/2021 Miller
2021/0346174 A1 11/2021 Flint
2021/0353428 A1 11/2021 Predick
2021/0378832 A1 12/2021 Altarac
2021/0378833 A1 12/2021 Gray
2022/0015923 A1* 1/2022 Shoshtaev ............. A61F 2/4611
2022/0104951 A1 4/2022 Predick
2022/0125596 A1 4/2022 Valkoun
2022/0133379 A1 5/2022 Nayet
2022/0133492 A1 5/2022 Josse
2022/0133496 A1 5/2022 Dewey
2022/0133497 A1 5/2022 Dewey
2022/0133498 A1 5/2022 Josse
2022/0133499 A1 5/2022 Josse
2022/0133503 A1 5/2022 Nayet
2022/0160515 A1 5/2022 Bougere
2022/0168116 A1 6/2022 Yadav
2022/0183854 A1 6/2022 Altarac
2022/0211512 A1* 7/2022 Berry ...................... A61F 2/447
2022/0265440 A1 8/2022 Lauf
2022/0339002 A1 10/2022 Freedman
2022/0387184 A1 12/2022 Josse
2022/0387190 A1 12/2022 Klausman
2022/0409388 A1 12/2022 Barfield
2023/0018019 A1 1/2023 Protopsaltis
2023/0023033 A1 1/2023 Eisen
2023/0026598 A1 1/2023 Weiman
2023/0060949 A1 3/2023 Ahn
2023/0072719 A1 3/2023 Rogers
2023/0095997 A1 3/2023 Ahn
2023/0114356 A1* 4/2023 Kang .................. A61F 2/30749
623/17.16
2023/0165687 A1 6/2023 Barrus
2023/0172724 A1 6/2023 Hansen
2023/0172726 A1* 6/2023 Krawiec ................ A61B 34/30
623/17.15
2023/0233333 A1 7/2023 Linares
2023/0277330 A1 9/2023 Stiefferman
2024/0307191 A1* 9/2024 Siccardi ................ A61F 2/4455
2025/0268722 A1* 8/2025 Emstad ..................... A61F 2/30
2025/0375298 A1* 12/2025 Casey ................. A61F 2/30942

FOREIGN PATENT DOCUMENTS

EP 2931183 B1 5/2018
EP 3421013 A1 1/2019
EP 2777632 B1 4/2020
EP 2830542 B1 10/2021
EP 3030198 B1 12/2021
EP 3485850 B1 9/2023
EP 3614974 B1 11/2024
EP 3614975 B1 11/2024
WO WO2013152257 A1 10/2013
WO WO2016069796 A1 5/2016
WO WO2019022976 A1 1/2019
WO WO2020068445 A1 4/2020
WO WO2020252040 A1 12/2020

* cited by examiner

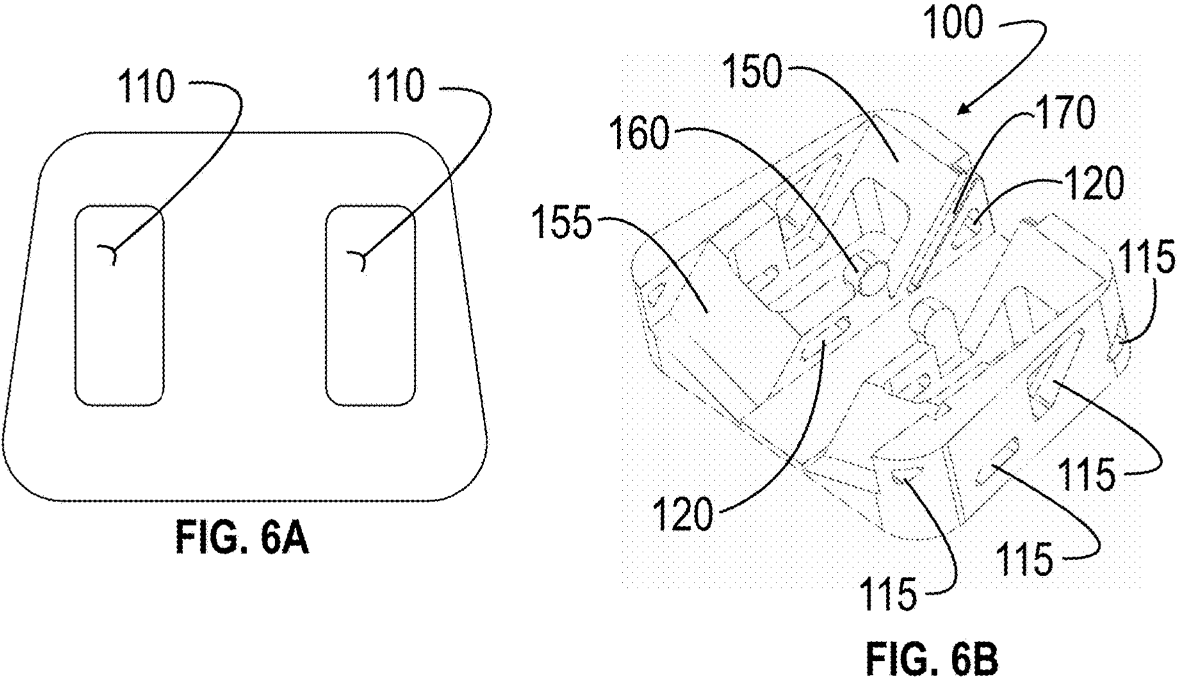
FIG. 6A
FIG. 6B
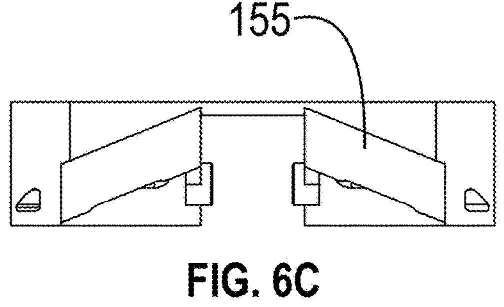
FIG. 6C
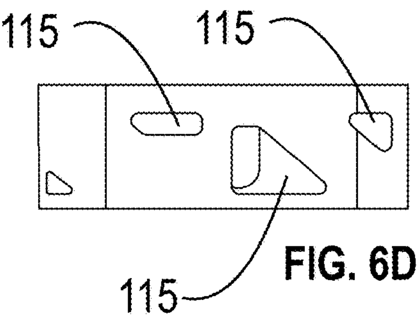
FIG. 6D

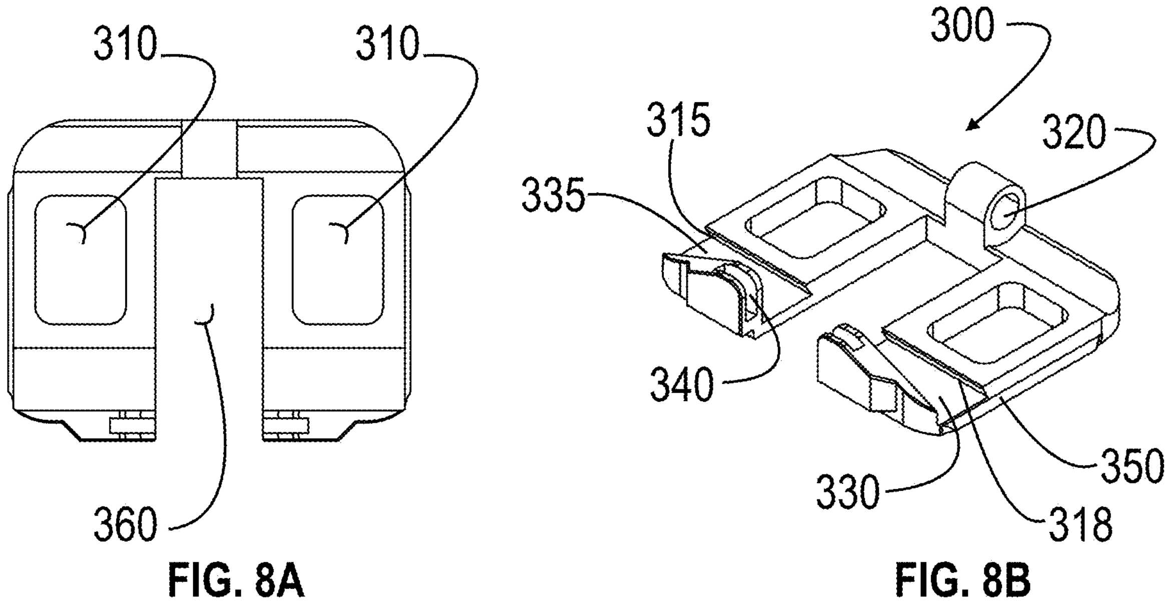
FIG. 8A
FIG. 8B
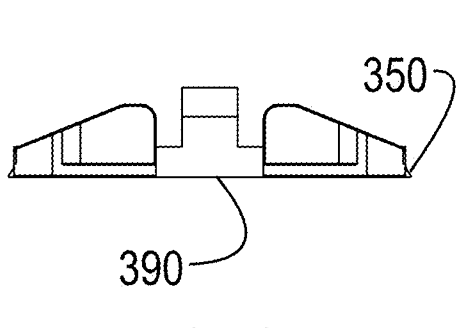
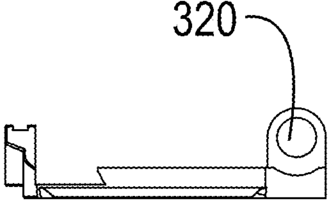
FIG. 8C
FIG. 8D

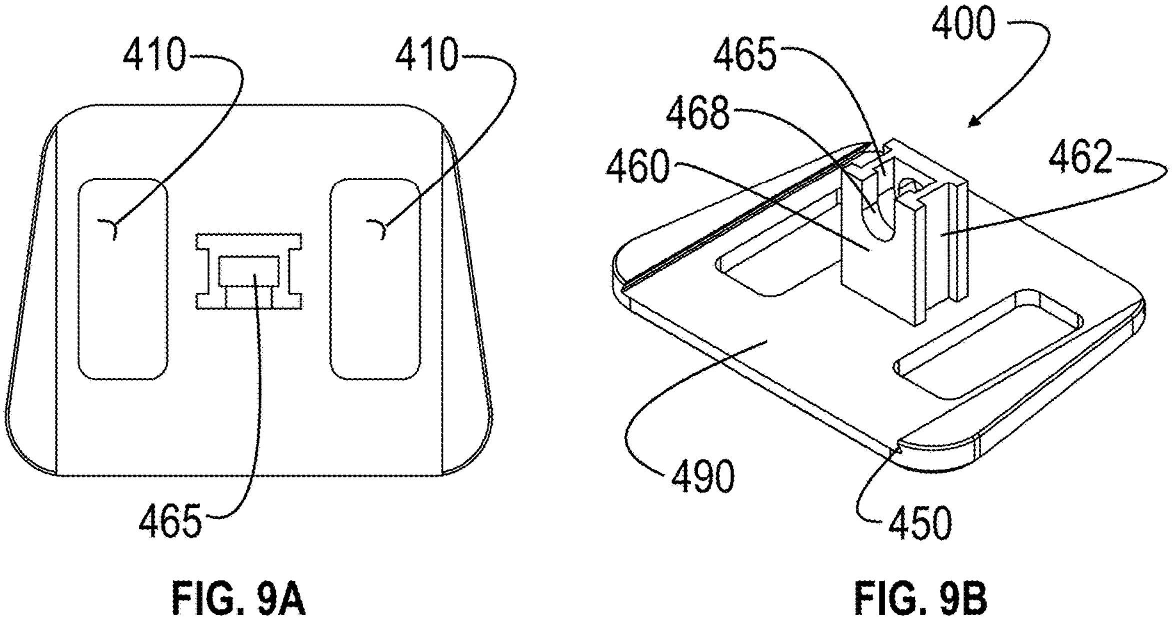
FIG. 9A
FIG. 9B
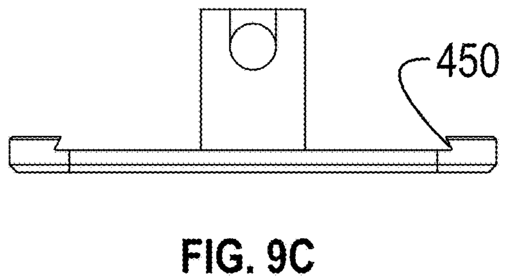
FIG. 9C
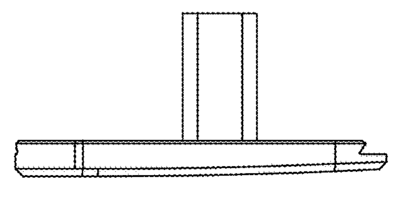
FIG. 9D

EXPANDABLE INTERVERTEBRAL IMPLANT

CROSS-REFERENCE TO RELATED APPLICATIONS

The present disclosure claims the benefit of U.S. Provisional Patent Application Ser. No. 63/541,798, filed on Sep. 30, 2023 entitled EXPANDABLE INTERVERTEBRAL IMPLANT, which is incorporated by reference as though set forth herein in its entirety.

TECHNICAL FIELD

The present disclosure relates to systems and methods for use in orthopedic surgery. More specifically, the present disclosure relates to expandable intervertebral implant systems and surgical methods.

SUMMARY

The various systems and methods of the present disclosure have been developed in response to the present state of the art, and in particular, in response to the problems and needs in the art that have not yet been fully solved by currently available intervertebral implants and surgical methods.

In some embodiments, an expandable intervertebral implant may include a superior plate configured to engage a superior vertebra, an inferior plate configured to engage an inferior vertebra, wherein the inferior plate is spaced apart from the superior plate by a gap, one or more first sliders moveable along a first direction to urge linear expansion of the gap, and one or more second sliders moveable along a second direction, nonparallel to the first direction, to urge angular expansion of the gap.

In the expandable intervertebral implant of any preceding paragraph, the first direction may be generally anterior-posterior, and the second direction may be generally medial-lateral.

In the expandable intervertebral implant of any preceding paragraph, the one or more second sliders may include a first second slider configured to move along the second direction and a second second slider configured to move along a direction opposite the second direction.

In the expandable intervertebral implant of any preceding paragraph, the one or more second sliders may not contact the superior plate or the inferior plate.

In the expandable intervertebral implant of any preceding paragraph, each of the one or more first sliders may be configured to urge linear expansion of the gap through movement in a single direction.

In the expandable intervertebral implant of any preceding paragraph, the expandable intervertebral implant may further include a bevel gear mechanism configured to actuate movement of the one or more second sliders along the second direction. The bevel gear mechanism may include a turnbuckle having a first axis of rotation and a bevel gear having a second axis of rotation. The first axis of rotation may be perpendicular to the second axis of rotation and the turnbuckle may be threadably connected to each of the one or more second sliders.

In the expandable intervertebral implant of any preceding paragraph, each of the one or more second sliders may be moveable transverse to an anterior-posterior direction to urge expansion of the gap.

In the expandable intervertebral implant of any preceding paragraph, the one or more first sliders may be moveable independently of motion of the one or more second sliders, such that the linear expansion of the gap may be independent of the angular expansion of the gap.

In the expandable intervertebral implant of any preceding paragraph, actuation of the linear expansion of the gap may occur before or after actuation of the angular expansion of the gap.

In some embodiments, an expandable intervertebral implant may include a superior plate configured to engage a superior vertebra, an inferior plate configured to engage an inferior vertebra, wherein the inferior plate is spaced apart from the superior plate by a gap, and a first slider moveable transverse to an anterior-posterior direction to urge expansion of the gap.

In the expandable intervertebral implant of any preceding paragraph, the expandable intervertebral implant may further include a second slider moveable in a direction opposite to the first slider to urge expansion of the gap.

In the expandable intervertebral implant of any preceding paragraph, the first slider may not contact the superior plate or the inferior plate.

In the expandable intervertebral implant of any preceding paragraph, the expandable intervertebral implant may further include a bevel gear mechanism configured to actuate movement of the first slider. The bevel gear mechanism may include a turnbuckle having a first axis of rotation and a bevel gear having a second axis of rotation. The first axis of rotation may be perpendicular to the second axis of rotation and the turnbuckle may be threadably connected to the first slider and the second slider.

In some embodiments, an expandable intervertebral implant may include a superior plate configured to engage a superior vertebra, an inferior plate configured to engage an inferior vertebra, wherein the inferior plate is spaced apart from the superior plate by a gap, and an expansion mechanism, configured to urge linear expansion and angular expansion of the gap, including a height wedge top coupled with the superior plate and a height wedge bottom coupled with the inferior plate. The height wedge top may be configured to remain parallel to the superior plate during linear expansion and angular expansion of the gap, and the height wedge bottom may be configured to remain parallel to the inferior plate during linear expansion and angular expansion of the gap.

In the expandable intervertebral implant of any preceding paragraph, the height wedge top may be rotatably coupled to the height wedge bottom.

In the expandable intervertebral implant of any preceding paragraph, the height wedge top may be translatable with respect to the superior plate in an inferior-superior direction and an anterior-posterior direction.

In the expandable intervertebral implant of any preceding paragraph, the expansion mechanism may further include one or more first sliders moveable along a first direction to urge linear expansion of the gap, and one or more second sliders moveable along a second direction, nonparallel to the first direction, to urge angular expansion of the gap.

In the expandable intervertebral implant of any preceding paragraph, the expandable intervertebral implant may further include a bevel gear mechanism configured to actuate movement of the one or more second sliders along the second direction. The bevel gear mechanism may include a turnbuckle having a first axis of rotation and a bevel gear having a second axis of rotation. The first axis of rotation may be perpendicular to the second axis of rotation and the turnbuckle may be threadably connected to each of the one or more second sliders.

In the expandable intervertebral implant of any preceding paragraph, the one or more second sliders may not contact the superior plate or the inferior plate.

In the expandable intervertebral implant of any preceding paragraph, the one or more first sliders may be moveable independently of motion of the one or more second sliders such that the linear expansion of the gap may be independent of the angular expansion of the gap.

These and other features and advantages of the present disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through the use of accompanying drawings.

BACKGROUND

Intervertebral disc degeneration and associated spinal disorders present significant clinical challenges, often leading to chronic pain and reduced mobility in affected individuals. Current surgical interventions primarily involve spinal fusion techniques or the use of fixed-size intervertebral implants. While these approaches aim to stabilize the spine and alleviate symptoms, they often limit natural spinal motion and may contribute to complications such as adjacent segment disease.

Fixed-size intervertebral implants currently available on the market vary in design and material composition but share common limitations. These implants require precise pre-operative sizing and may necessitate intraoperative adjustments to ensure proper fit within the disc space. Surgeons may also face challenges in adapting these implants to individual patient anatomy and achieving optimal alignment post-implantation. Moreover, the complexity of implantation procedures can prolong surgery times and recovery periods for patients.

Recognizing these challenges, there is a growing demand for intervertebral implants that offer greater versatility and precision in surgical application. An ideal solution would provide adjustable sizing capabilities intraoperatively, facilitating tailored fitment to varying disc spaces and spinal geometries. Such advancements could potentially improve surgical outcomes, minimize recovery times, and reduce the incidence of postoperative complications associated with current implant technologies.

SUMMARY

The various systems and methods of the present disclosure have been developed in response to the present state of the art, and in particular, in response to the problems and needs in the art that have not yet been fully solved by currently available acetabular prosthetic systems and methods.

These and other features and advantages of the present disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through the use of accompanying drawings.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the disclosure will be described with additional specificity and detail through use of the accompanying drawings in which:

FIG. 6A is a top view of a superior plate of an expandable intervertebral implant according to an embodiment;

FIG. 6B is a perspective view of the superior plate of the expandable intervertebral implant of FIG. 6A;

FIG. 6C is a front view of the superior plate of the expandable intervertebral implant of FIG. 6A;

FIG. 6D is a side view of the superior plate of the expandable intervertebral implant of FIG. 6A;

FIG. 8A is a top view of a height wedge bottom of an expandable intervertebral implant according to an embodiment;

FIG. 8B is a perspective view of the height wedge bottom of the expandable intervertebral implant of FIG. 8A;

FIG. 8C is a front view of the height wedge bottom of the expandable intervertebral implant of FIG. 8A;

FIG. 8D is a side view of the height wedge bottom of the expandable intervertebral implant of FIG. 8A;

FIG. 9A is a top view of an inferior plate of an expandable intervertebral implant according to an embodiment;

FIG. 9B is a perspective view of the inferior plate of the expandable intervertebral implant of FIG. 9A;

FIG. 9C is a front view of the inferior plate of the expandable intervertebral implant of FIG. 9A;

FIG. 9D is a side view of the inferior plate of the expandable intervertebral implant of FIG. 9A;

DETAILED DESCRIPTION

Figures 1A, 1B, 1C, 1D, 1E:
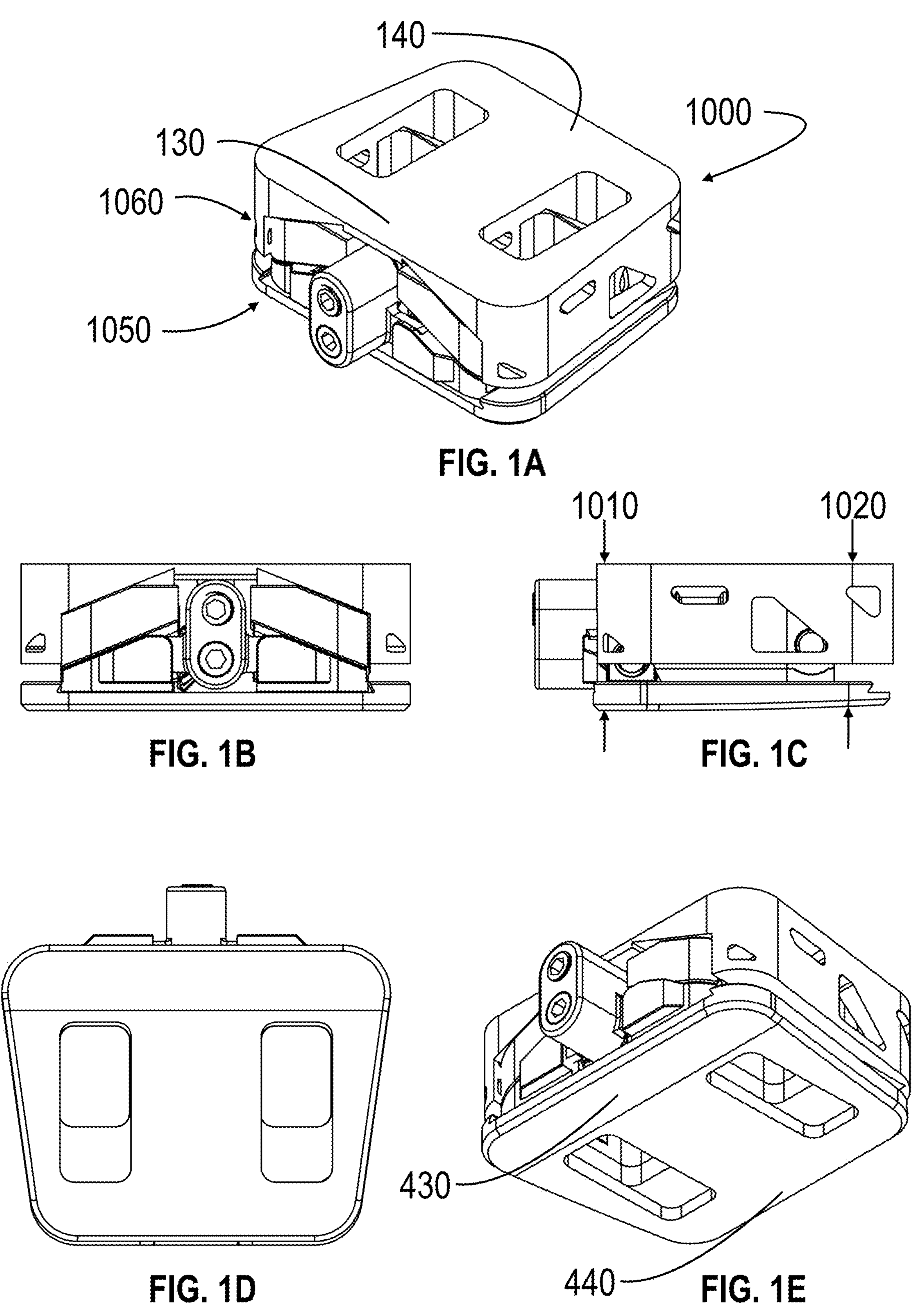
FIG. 1A is a perspective view of an expandable intervertebral implant according to an embodiment of the present disclosure.
FIG. 1B is a front view of the expandable intervertebral implant of FIG. 1A.
FIG. 1C is a side view of the expandable intervertebral implant of FIG. 1A.
FIG. 1D is a bottom view of the expandable intervertebral implant of FIG. 1A.
FIG. 1E is a bottom view of the expandable intervertebral implant of FIG. 1A.

Exemplary embodiments of the present disclosure will be best understood by reference to the drawings, wherein like parts are designated by like numerals throughout. It will be readily understood that the components of the present disclosure, as generally described and illustrated in the drawings, could be arranged, and designed in a wide variety of different configurations. Thus, the following more detailed description of the embodiments of the devices, systems, and methods, as represented in the drawings, is not intended to limit the scope of the present disclosure but is merely representative of exemplary embodiments of the present disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

Standard medical planes of reference and descriptive terminology are employed in this specification. While these terms are commonly used to refer to the human body, certain terms are applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot. Varus means deviation of the distal part of the leg below the knee inward, resulting in a bowlegged appearance. Valgus means deviation of the distal part of the leg below the knee outward, resulting in a knock-kneed appearance.

The present disclosure relates to intervertebral implant devices, systems, and methods. Those skilled in the art will recognize that the following description is merely illustrative of the principles of the technology, which may be applied in various ways to provide many alternative embodiments. The present disclosure is devices for an anterior lumbar interbody fusion (ALIF) for the purposes of illustrating the concepts of the present design. However, it will be understood that other variations and uses are contemplated including, but not limited to, devices for a posterior lumbar interbody fusion (PLIF), devices for transforaminal lumbar interbody fusion (TLIF), devices for interbody fusion of the thoracic spine, devices for interbody fusion of the cervical spine, etc.

FIG. 1A is a perspective view of an expandable intervertebral implant 1000 according to an embodiment. The expandable intervertebral implant 1000 may be configured to be implanted within a spinal disc space following a discectomy procedure during an anterior lumbar interbody fusion (ALIF) procedure. The expandable intervertebral implant 1000 may be implanted between a superior vertebra and an inferior vertebra to support fusion of the vertebral bodies. The expandable intervertebral implant 1000 may be configured to include a superior plate 100 and an inferior plate 400. The superior plate 100 may include a superior anterior portion 130 and a superior posterior portion 140. The inferior plate 400 may include an inferior anterior portion 430 and an inferior posterior portion 440.

The expandable intervertebral implant 1000 may include a superior plate 100 configured to engage a superior vertebra; an inferior plate 400 configured to engage an inferior vertebra, wherein the inferior plate is spaced apart from the superior plate by a gap; one or more first sliders 1050 moveable along a first direction to urge linear expansion of the gap; and one or more second sliders 1060 moveable along a second direction, nonparallel to the first direction, to urge angular expansion of the gap. The one or more first sliders 1050 may include a height wedge top 200 and a height wedge bottom 300. The one or more second sliders 1060 may include a first angle wedge 500 and a second angle wedge 550. The expandable intervertebral implant 1000 may be configured so that movement of the one or more first slider 1050 in a single direction may result in linear expansion of the expandable intervertebral implant 1000.

Additionally, or alternatively, the expandable intervertebral implant 1000 may include a superior plate 100 configured to engage a superior vertebra; an inferior plate 400 configured to engage an inferior vertebra, wherein the inferior plate is spaced apart from the superior plate by a gap; one or more first sliders 1050 moveable transverse to an anterior-posterior direction to urge expansion of the gap.

FIG. 1B is a front view of the expandable intervertebral implant 1000, FIG. 1C is a side view of the expandable intervertebral implant 1000, FIG. 1D is a bottom view of the expandable intervertebral implant 1000, and FIG. 1E is a bottom view of the expandable intervertebral implant 1000. The expandable intervertebral implant 1000 may include an anterior height 1010 and a posterior height 1020. The anterior height 1010 may be the distance, in a superior-inferior plane, between the superior anterior portion 130 and the inferior anterior portion 430. The posterior height 1020 may be the distance, in the superior-inferior plane, between the superior posterior portion 140 and the inferior posterior portion 440.

The expandable intervertebral implant 1000 may be configured to include an un-expanded state. In the un-expanded state, the anterior height 1010 may be generally equal to the posterior height 1020. Additionally, the expandable intervertebral implant 1000 may be configured for multiple height size variations ranging from 8 mm to 20 mm in the un-expanded state. In some embodiments, the expandable intervertebral implant 1000 may be configured for multiple angular variations ranging from 0° to 20° in the un-expanded state.

In some embodiments, the expandable intervertebral implant 1000 may be configured to be placed into a disc space in an un-expanded state and expanded in-situ to restore an anatomical intervertebral disc height and angle between a superior vertebra and an inferior vertebra. In some embodiments, the expandable intervertebral implant 1000 may be configured to expand in height so that the anterior height 1010 and the posterior height 1020 increase at the same rate as each other during the expansion process. In some embodiments, the expandable intervertebral implant 1000 may be configured to expand at an angle whereby the anterior height 1010 is increased and the posterior height 1020 remains generally unchanged.

The expandable intervertebral implant 1000 may be configured so that the right side of the expandable intervertebral implant 1000 and left side of the expandable intervertebral implant 1000 may be expanded independently of each other in a medial-lateral direction.

The expandable intervertebral implant 1000 may further be configured so that linear expansion of the expandable intervertebral implant 1000 may be independent of angular expansion of the expandable intervertebral implant 1000. Additionally, or alternatively, the expandable intervertebral implant 1000 may further be configured so that actuation of the linear expansion of the expandable intervertebral implant 1000 may be independent of actuation of the angular expansion of the expandable intervertebral implant 1000.

In some embodiments, the expandable intervertebral implant 1000 may be configured so that the linear expansion, whereby the anterior height 1010 and the posterior height 1020 increase at generally the same rate as each other during the expansion process, may be actuated by a first means; and the angular expansion, whereby the anterior height 1010 is increased and the posterior height remains generally unchanged, may be actuated by a second means. In some embodiments the first means of actuation and the second means of actuation are distinct and may be engaged independently of each other. In some embodiments, the first means of actuation and the second means of actuation may be engaged in any sequence. In an embodiment, actuation of the linear expansion of the gap may occur before or after actuation of the angular expansion of the gap.

Figure 2:
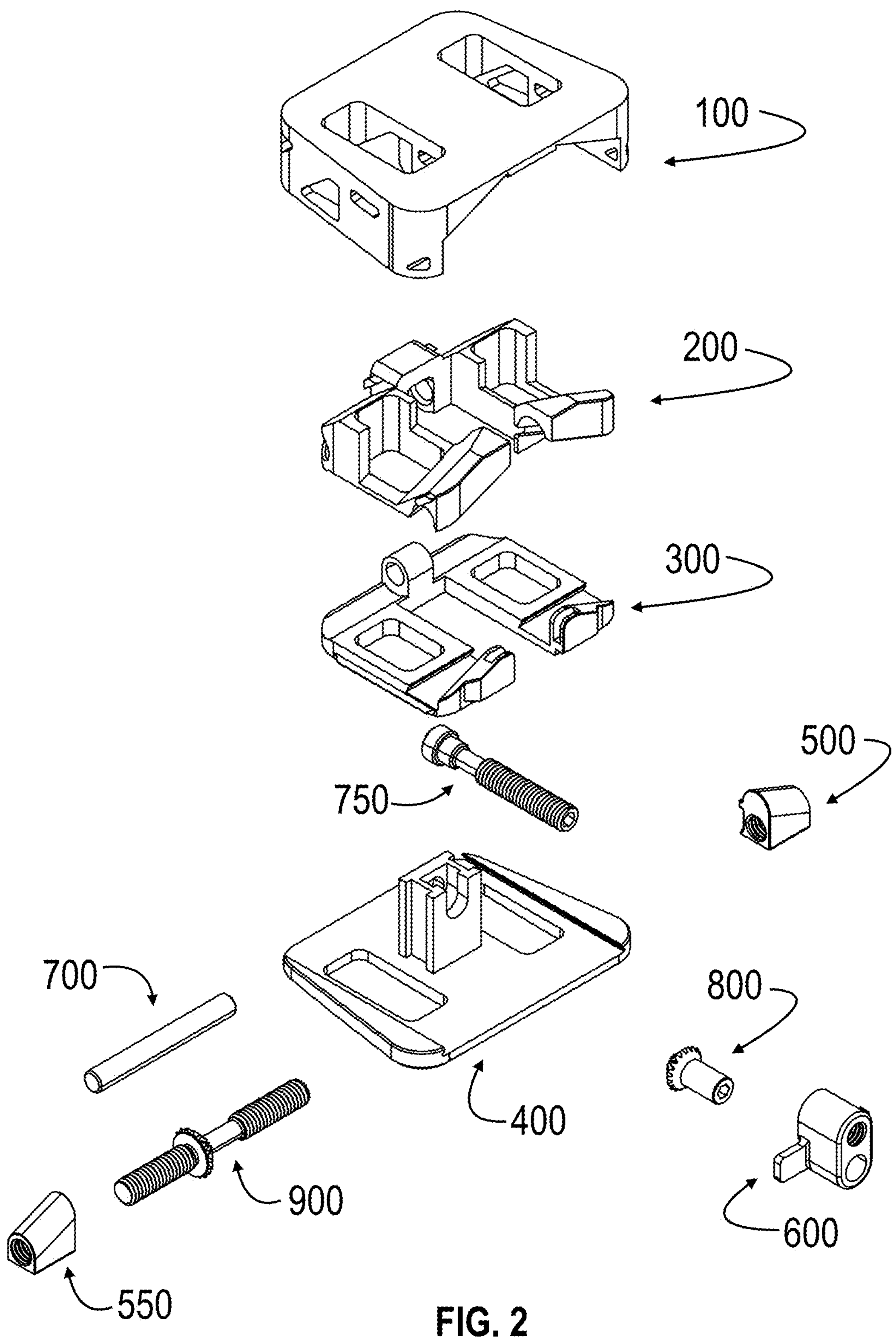
FIG. 2 is an exploded view of the expandable intervertebral implant of FIG. 1A.

FIG. 2 is an exploded view of the expandable intervertebral implant 1000. the expandable intervertebral implant 1000 may include a superior plate 100; a height wedge top 200; a height wedge bottom 300; an inferior plate 400; a first angle wedge 500; a second angle wedge 550; a pusher 600; a height wedge pin 700; a height shaft 750; a bevel gear component 800; and a turnbuckle 900.

Figure 3A:
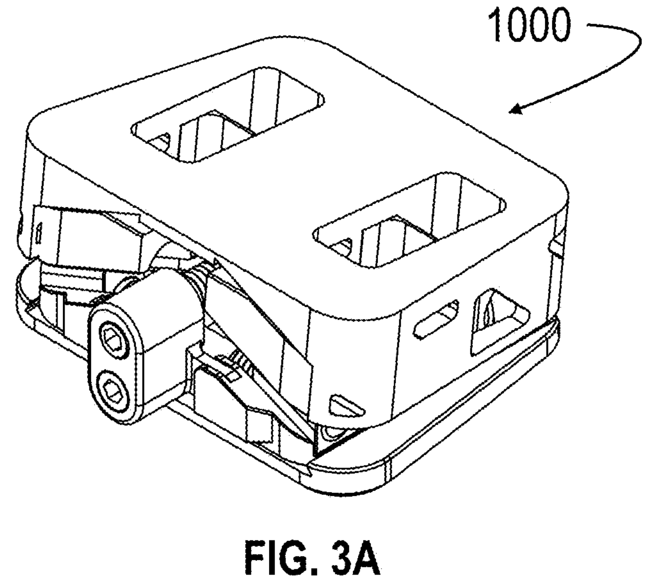
FIG. 3A is a perspective view of the expandable intervertebral implant of FIG. 1A in an alternate expanded state.
Figure 3B:
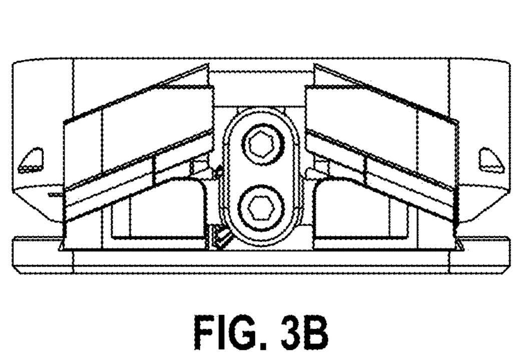
FIG. 3B is a front view of the expandable intervertebral implant of FIG. 1A in an alternate expanded state.
Figure 3C:
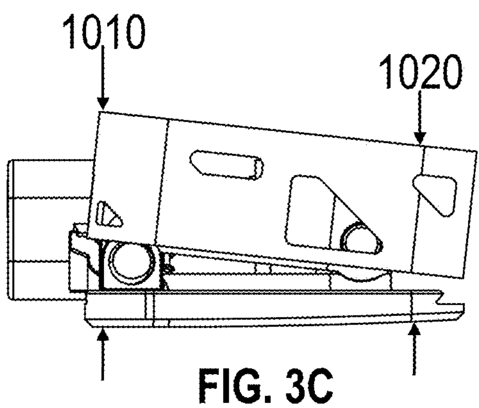
FIG. 3C is a side view of the expandable intervertebral implant of FIG. 1A in an alternate expanded state.

FIG. 3A is a perspective view of the expandable intervertebral implant 1000 in an alternate expanded state, FIG. 3B is a front view of the expandable intervertebral implant 1000 in an alternate expanded state, and FIG. 3C is a side view of the expandable intervertebral implant 1000 in an alternate expanded state. The expandable intervertebral implant 1000 may be configured to be angularly expandable to generally match the lordotic angle of a superior vertebra and an inferior vertebra. The expandable intervertebral implant 1000 may be configured wherein angular expansion increases the anterior height 1010 without generally increasing the posterior height 1020. In another embodiment, the expandable intervertebral implant 1000 may be configured for a posterior lumbar interbody fusion (PLIF) procedure, wherein angular expansion increases the posterior height 1020 without generally increasing the anterior height 1010. The range of angular expansion may be between 0° and 10°.

Figure 4A:
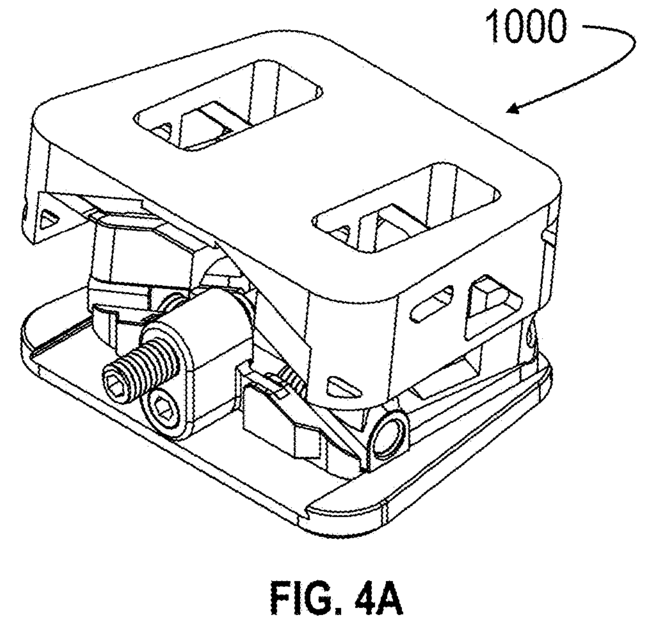
FIG. 4A is a perspective view of the expandable intervertebral implant of FIG. 1A in an alternate expanded state.
Figure 4B:
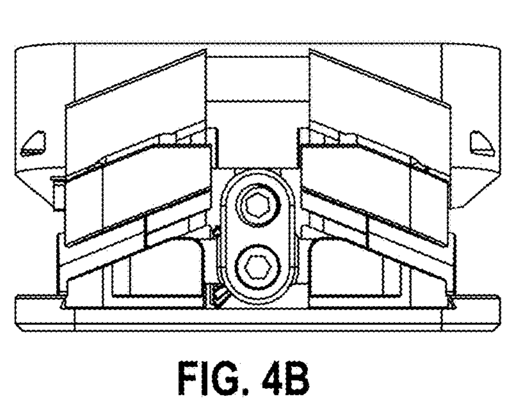
FIG. 4B is a front view of the expandable intervertebral implant of FIG. 1A in an alternate expanded state.
Figure 4C:
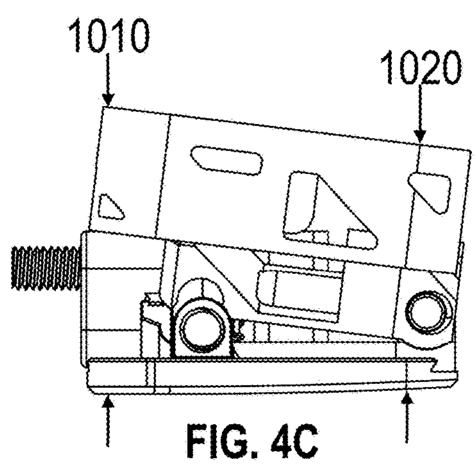
FIG. 4C is a side view of the expandable intervertebral implant of FIG. 1A in an alternate expanded state.

FIG. 4A is a perspective view of the expandable intervertebral implant 1000 in an alternate expanded state, FIG. 4B is a front view of the expandable intervertebral implant 1000 in an alternate expanded state, and FIG. 4C is a side view of the expandable intervertebral implant 1000 in an alternate expanded state. The expandable intervertebral implant 1000 may be configured to be angularly expandable to generally match the lordotic angle of a superior vertebra and an inferior vertebra; and linearly expandable to increase the height of the implant. The expandable intervertebral implant 1000 may be configured wherein angular expansion increases the anterior height 1010 without generally increasing the posterior height 1020; and linear expansion increases both the anterior height 1010 and the posterior height 1020. In an embodiment, actuation of angular expansion may be independent of actuation of linear expansion.

Figure 5A:
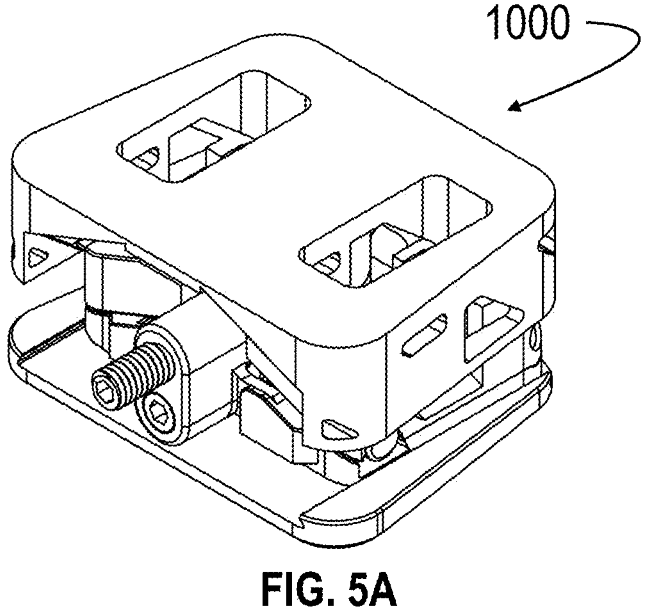
FIG. 5A is a perspective view of the expandable intervertebral implant of FIG. 1A in an alternate expanded state.
Figure 5B:
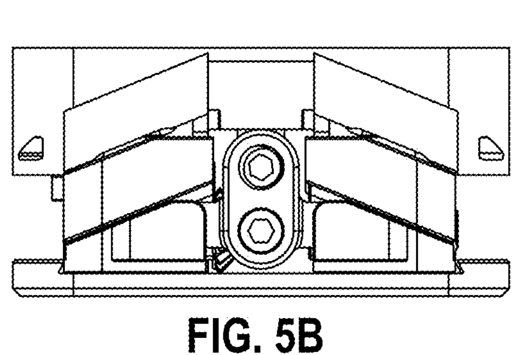
FIG. 5B is a front view of the expandable intervertebral implant of FIG. 1A in an alternate expanded state.
Figure 5C:
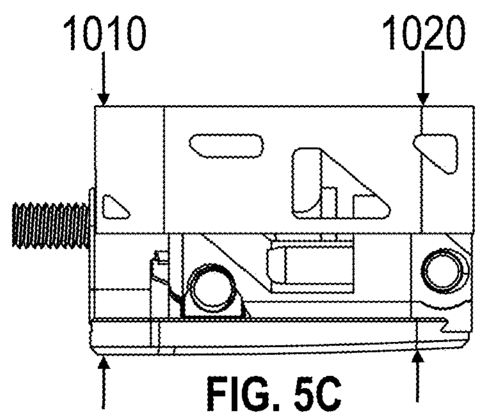
FIG. 5C is a side view of the expandable intervertebral implant of FIG. 1A in an alternate expanded state.

FIG. 5A is a perspective view of the expandable intervertebral implant 1000 in an alternate expanded state, FIG. 5B is a front view of the expandable intervertebral implant 1000 in an alternate expanded state, and FIG. 5C is a side view of the expandable intervertebral implant 1000 in an alternate expanded state. The expandable intervertebral implant 1000 may be configured to be linearly expandable to increase the height of the implant. The expandable intervertebral implant 1000 may be configured wherein linear expansion increases both the anterior height 1010 and the posterior height 1020. The range of linear expansion may be between 0 mm and 8 mm.

FIG. 6A is a top view of a superior plate 100 of an expandable intervertebral implant 1000 according to an embodiment. FIG. 6B is a perspective view of the superior plate 100 of the expandable intervertebral implant 1000, FIG. 6C is a front view of the superior plate 100 of the expandable intervertebral implant 1000, and FIG. 6D is a side view of the superior plate 100 of the expandable intervertebral implant 1000. The superior plate 100 may be configured to engage a superior vertebra. The superior plate 100 may include a plurality of superior plate apertures 110 to allow bone growth between a superior vertebra and an inferior vertebra through the expandable intervertebral implant 1000. The superior plate 100 may further include a plurality of side apertures 115. The superior plate 100 may be configured to receive bone graft material to facilitate bone ingrowth. The superior plate 100 may further include a plurality of internal apertures 120. The plurality of internal apertures may be configured to facilitate bone ingrowth within the expandable intervertebral implant 1000. The superior plate 100 may include one or more first angled portions 150 and one or more second angled portions 155. The one or more first angled portions 150 may be configured to slidably engage one or more third angled portions 250. The one or more second angled portions 155 may be configured to slidably engage one or more fourth angled portions 255. The one or more first angled portions 150 and the one or more second angled portions 155 may be configured so that an applied force in a posterior direction from the one or more third angled portions 250 and one or more fourth angled portions 255 results in translation of the superior plate 100. The superior plate 100 may further include one or more bosses 160 configured to slidably engage one or more post channels 462. The one or more bosses may further be configured to allow translation of the superior plate 100 in a superior-inferior direction but not allow translation of the superior plate 100 in a medial-lateral direction or an anterior-posterior direction.

The superior plate 100 may be configured to be slidably captive with other components of the expandable intervertebral implant 1000 which may prevent the superior plate 100 from separating from the expandable intervertebral implant 1000. The superior plate 100 may include one or more angled channels 170. The one or more angled channels 170 may be configured to slidably engage one or more angled tabs 270 of a height wedge top 200. The one or more angled channels 170 may be configured so that an applied force in a posterior direction from the one or more angled tabs 270 results in translation of the superior plate 100. The one or more first angled portions 150, the one or more second angled portions 155, and the one or more angled channels 170 may be configured to have generally similar angles relative to the top surface of the superior plate 100.

Figure 7A:
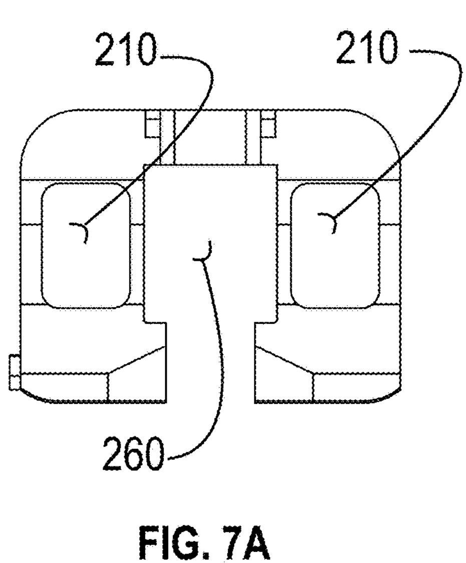
FIG. 7A is a top view of a height wedge top of an expandable intervertebral implant according to an embodiment.
Figure 7A:
Figure 7B:
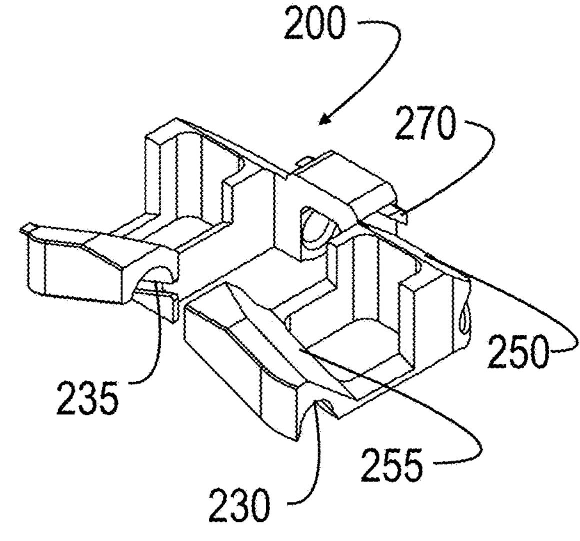
FIG. 7B is a perspective view of the height wedge top of the expandable intervertebral implant of FIG. 7A.
Figure 7C:
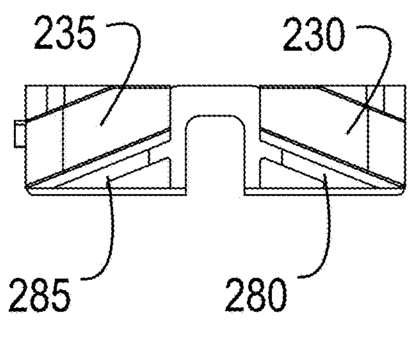
FIG. 7C is a front view of the height wedge top of the expandable intervertebral implant of FIG. 7A.
Figure 7D:
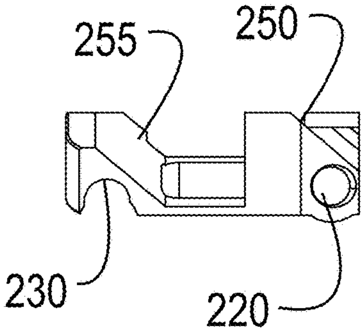
FIG. 7D is a side view of the height wedge top of the expandable intervertebral implant of FIG. 7A.

FIG. 7A is a top view of a height wedge top 200 of an expandable intervertebral implant 1000 according to an embodiment. FIG. 7B is a perspective view of the height wedge top 200 of the expandable intervertebral implant 1000, FIG. 7C is a front view of the height wedge top 200 of the expandable intervertebral implant 1000, and FIG. 7D is a side view of the height wedge top 200 of the expandable intervertebral implant 1000. The height wedge top 200 may be configured to slidably engage a superior plate 100 so that translational movement of the superior plate 100 is relative to the height wedge top 200. The height wedge top 200 may be translatable with respect to the superior plate 100 in an inferior-superior direction and an anterior-posterior direction The height wedge top 200 may include a plurality of height wedge top apertures 210 to allow bone growth between a superior vertebra and an inferior vertebra through the expandable intervertebral implant 1000.

FIG. 8A is a top view of a height wedge bottom 300 of an expandable intervertebral implant 1000 according to an embodiment. FIG. 8B is a perspective view of the height wedge bottom 300 of the expandable intervertebral implant 1000, FIG. 8C is a front view of the height wedge bottom 300 of the expandable intervertebral implant 1000, and FIG. 8D is a side view of the height wedge bottom 300 of the expandable intervertebral implant 1000. The height wedge bottom 300 may be configured to slidably engage an inferior plate 400. The height wedge bottom 300 may include a plurality of height wedge bottom apertures 310 to allow bone growth between a superior vertebra and an inferior vertebra through the expandable intervertebral implant 1000.

The height wedge top 200 may be rotatably coupled to the height wedge bottom 300. The height wedge top 200 may include a first rotation aperture 220 configured to receive a height wedge pin 700. The height wedge bottom 300 may include a second rotation aperture 320 configured to receive the height wedge pin 700.

The height wedge top 200 may be configured to rotate with respect to the height wedge bottom 300. The height wedge top 200 may include a first arced channel 230 and a second arced channel 235. The second arced channel 235 may be configured as a mirror image of the first arced channel 230, mirrored about a medial-lateral plane. The first arced channel 230 and the second arced channel 235 may each include a groove with a semi-circular surface. The first arced channel 230 may be oriented at an angle between 1 degree and 89 degrees with respect to the base of the height wedge top 200.

FIG. 9A is a top view of an inferior plate 400 of an expandable intervertebral implant 1000 according to an embodiment. FIG. 9B is a perspective view of the inferior plate 400 of the expandable intervertebral implant 1000, FIG. 9C is a front view of the inferior plate 400 of the expandable intervertebral implant 1000, and FIG. 9D is a side view of the inferior plate 400 of the expandable intervertebral implant 1000. The inferior plate 400 may be configured to slidably engage a height wedge bottom 300. The inferior plate 400 may include a plurality of inferior plate apertures 410 to allow bone growth between a superior vertebra and an inferior vertebra through the expandable intervertebral implant 1000. The inferior plate 400 may include a top surface 490 configured to slidably engage a height wedge bottom surface 390. The inferior plate 400 may further include one or more second locating surfaces 450 configured to captively and slidably engage one or more first locating surfaces 350 of the height wedge bottom 300. The one or more second locating surfaces 450 and the one or more first locating surfaces 350 may be configured to allow sliding of the height wedge bottom 300 with respect to the inferior plate 400 in an anterior-posterior direction.

The inferior plate 400 may include a post 460 configured to extend through a height wedge bottom clearance portion 360 and a height wedge top clearance portion 260 to slidably engage a superior plate 100. The post 460 may include one or more post channels 462 configured to slidably engage one or more bosses 160 of a superior plate 100.

Figures 10A, 10B, 10C, 11A, 11B, 11C:
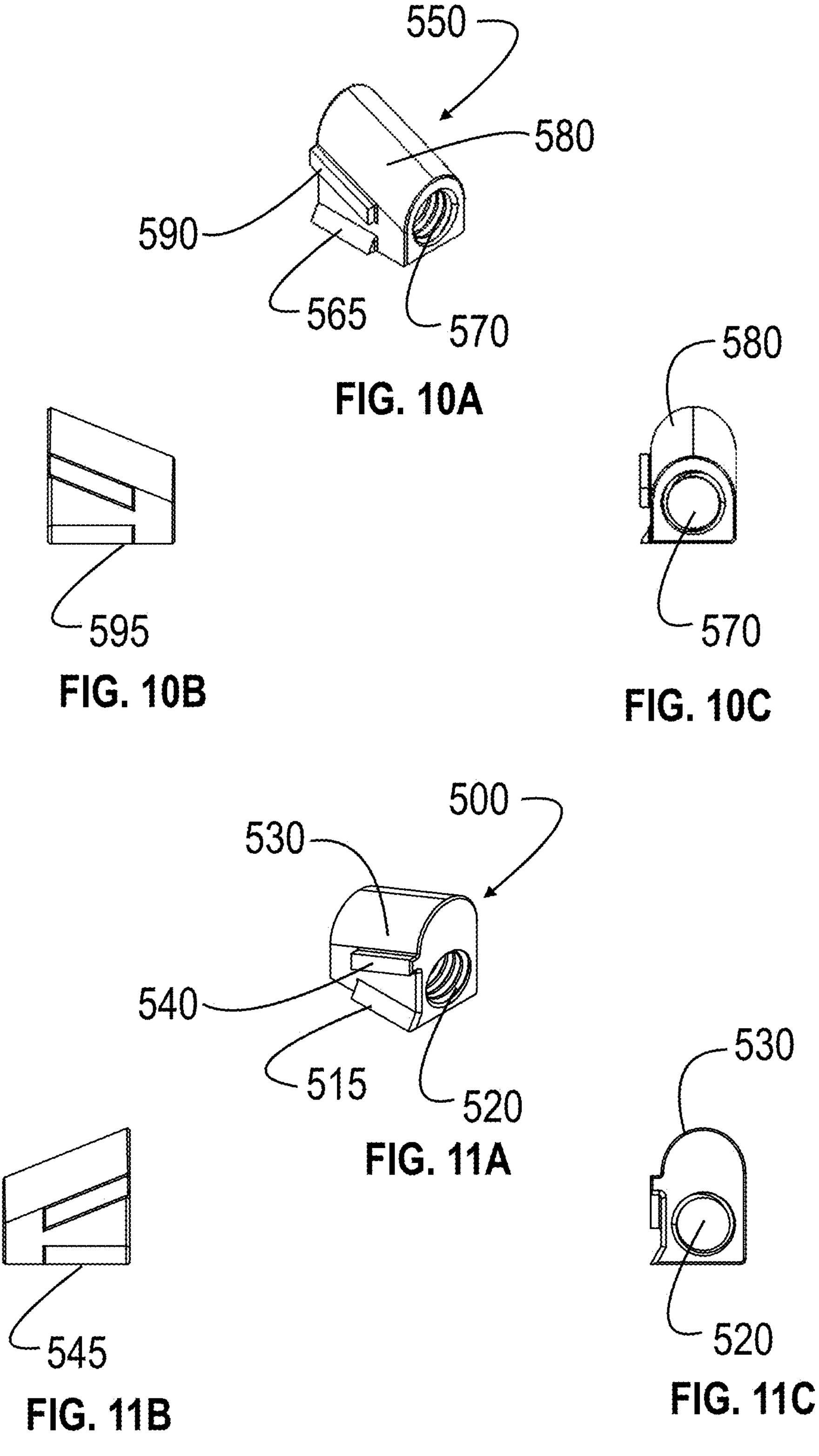
FIG. 10A is a perspective view of a second angle wedge of an expandable intervertebral implant according to an embodiment.
FIG. 10B is a front view of the second angle wedge of the expandable intervertebral implant of FIG. 10A.
FIG. 10C is a side view of the second angle wedge of the expandable intervertebral implant of FIG. 10A.
FIG. 11A is a perspective view of a first angle wedge of an expandable intervertebral implant according to an embodiment.
FIG. 11B is a front view of the first angle wedge of the expandable intervertebral implant of FIG. 11A.
FIG. 11C is a side view of the first angle wedge of the expandable intervertebral implant of FIG. 11A.

FIG. 10A is a perspective view of a second angle wedge 550 of an expandable intervertebral implant 1000 according to an embodiment. FIG. 10B is a front view of the second angle wedge 550 of the expandable intervertebral implant 1000 and FIG. 10C is a side view of the second angle wedge 550 of the expandable intervertebral implant 1000. The second angle wedge 550 may be configured to be slidably and captively connected to an inferior plate 400. Additionally, the second angle wedge 550 may be configured to apply a force in a superior direction to a height wedge top 200 when moved in a medial-lateral direction along the inferior plate 400. The second angle wedge 550 may include a second wedge bottom surface 595 configured to slidably engage a second straight channel 335. The second angle wedge 550 may include a third wedge locating surface 565 configured to slidably engage a second wedge locating surface 315 on a height wedge bottom 300. The third wedge locating surface 565 may be configured to allow sliding of the second angle wedge 550 with respect to the height wedge bottom 300 in a medial-lateral direction. The second angle wedge 550 may not contact the superior plate 100 or the inferior plate 400.

The second angle wedge 550 may include a second arced surface 580 configured to slidably engage a second arced channel 235. A profile of the second arced surface 580 may be configured to be complementary to a profile of the second arced channel 235. The second angle wedge 550 may include a second wedge tab 590 configured to slidably engage a second wedge channel 285 of a height wedge top 200.

FIG. 11A is a perspective view of a first angle wedge 500 of an expandable intervertebral implant 1000 according to an embodiment. FIG. 11B is a front view of the first angle wedge 500 of the expandable intervertebral implant 1000 and FIG. 11C is a side view of the first angle wedge 500 of the expandable intervertebral implant 1000. The first angle wedge 500 may be configured to be slidably and captively connected to an inferior plate 400. Additionally, the first angle wedge 500 may be configured to apply a force in a superior direction to a height wedge top 200 when moved in a medial-lateral direction along the inferior plate 400. The first angle wedge 500 may include a first wedge bottom surface 545 configured to slidably engage a first straight channel 330. The first angle wedge 500 may include a first wedge locating surface 515 configured to slidably engage a fourth wedge locating surface 318 on a height wedge bottom 300. The first wedge locating surface 515 may be configured to allow sliding of the first angle wedge 500 with respect to the height wedge bottom 300 in a medial-lateral direction. The first angle wedge 500 may not contact the superior plate 100 or the inferior plate 400.

The first angle wedge 500 may include a first arced surface 530 configured to slidably engage a first arced channel 230. A profile of the first arced surface 530 may be configured to be complementary to a profile of the first arced channel 230. The first angle wedge 500 may include a first wedge tab 540 configured to slidably engage a first wedge channel 280 of a height wedge top 200.

Figure 12A:
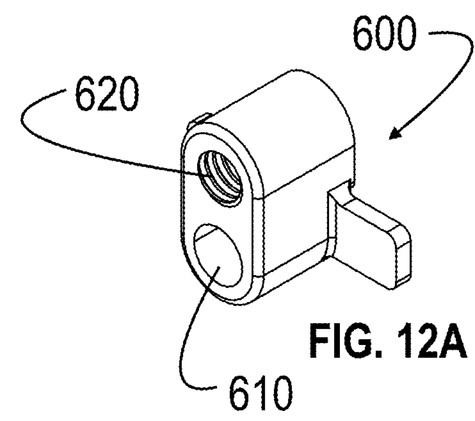
FIG. 12A is a perspective view of a pusher of an expandable intervertebral implant according to an embodiment.
Figure 12B:
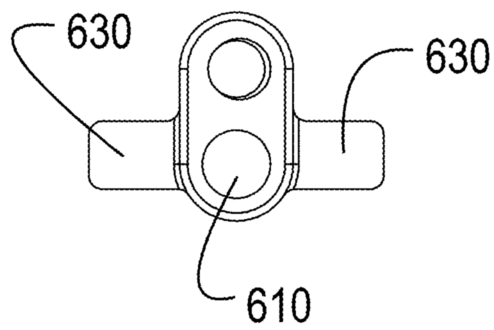
FIG. 12B is a front view of the pusher of the expandable intervertebral implant of FIG. 12A.
Figure 12B:
Figure 12C:
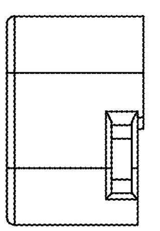
FIG. 12C is a side view of the pusher of the expandable intervertebral implant of FIG. 12A.

FIG. 12A is a perspective view of a pusher 600 of an expandable intervertebral implant 1000 according to an embodiment. FIG. 12B is a front view of the pusher 600 of the expandable intervertebral implant 1000 and FIG. 12C is a side view of the pusher 600 of the expandable intervertebral implant 1000. The pusher 600 may be configured to be part of an expansion mechanism. The pusher 600 may convert rotational motion of a height shaft 750 into linear motion of a height wedge bottom 300. The pusher 600 may include one or more tabs 630 configured to engage one or more slots 340 of a height wedge bottom 300. The one or more tabs 630 and the one or more slots 340 may be configured so that translation of the pusher 600 in an anterior-posterior direction results in generally equal translation of the height wedge bottom 300 in the same direction. The pusher 600 may include a first hole 610 configured to rotatably receive a bevel gear shaft 810. The pusher may further include a third threaded hole 620 configured to receive a threaded portion 760 of a height shaft 750.

Figure 13A:
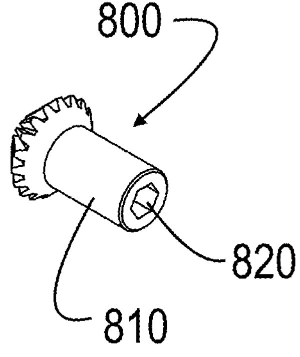
FIG. 13A is a perspective view of a bevel gear component of an expandable intervertebral implant according to an embodiment.
Figure 13B:
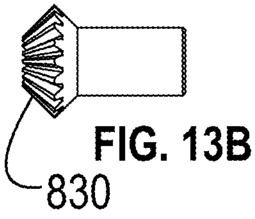
FIG. 13B is a front view of the bevel gear component of the expandable intervertebral implant of FIG. 13A.
Figure 13C:
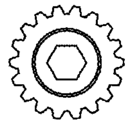
FIG. 13C is a side view of the bevel gear component of the expandable intervertebral implant of FIG. 13A.

FIG. 13A is a perspective view of a bevel gear component 800 of an expandable intervertebral implant 1000 according to an embodiment. FIG. 13B is a front view of the bevel gear component 800 of the expandable intervertebral implant 1000 and FIG. 13C is a side view of the bevel gear component 800 of the expandable intervertebral implant 1000. The bevel gear component 800 may be configured to rotatably engage a turnbuckle 900 to transfer rotational motion along a first axis to rotational motion along a second axis perpendicular to the first axis.

The bevel gear component 800 may include a bevel gear shaft 810 configured to rotatably engage a first hole 610 in a pusher 600. The bevel gear component 800 may further include a first bevel gear face 830 configured to engage a second bevel gear face 930 of a turnbuckle 900. The bevel gear component 800 may include a second female drive feature 820 configured to facilitate rotation of the bevel gear component 800 through engagement with a drive tool. The second female drive feature 820 may be configured as a hex, a hexalobe, a square or other non-circular profile known in the art.

In an embodiment, an actuation device, external to an expandable intervertebral implant 1000, may include a gear/turnbuckle mechanism configured to engage the expandable intervertebral implant 1000. The actuation device may be configured to removably engage the expandable intervertebral implant 1000. The actuation device may be configured to actuate height and/or angular expansion of the expandable intervertebral implant 1000. Additionally, the expandable intervertebral implant 1000 may be configured to retain the height and/or angular expansion driven by the actuation device.

Figure 14A:
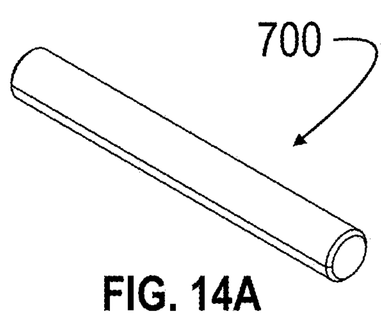
FIG. 14A is a perspective view of a height wedge pin of an expandable intervertebral implant according to an embodiment.
Figure 14B:
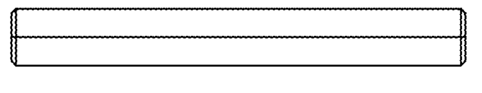
FIG. 14B is a front view of the height wedge pin of the expandable intervertebral implant of FIG. 14A.
Figure 14C:
FIG. 14C is a side view of the height wedge pin of the expandable intervertebral implant of FIG. 14A.

FIG. 14A is a perspective view of a height wedge pin 700 of an expandable intervertebral implant 1000 according to an embodiment. FIG. 14B is a front view of the height wedge pin 700 of the expandable intervertebral implant 1000 and FIG. 14C is a side view of the height wedge pin 700 of the expandable intervertebral implant 1000. The height wedge pin 700 may be configured to rotatably engage a first rotation aperture 220 of a height wedge top 200 and a second rotation aperture 320 of a height wedge bottom 300 to allow rotation of the height wedge top 200 with respect to the height wedge bottom 300 about the axis of the height wedge pin 700.

Figure 15A:
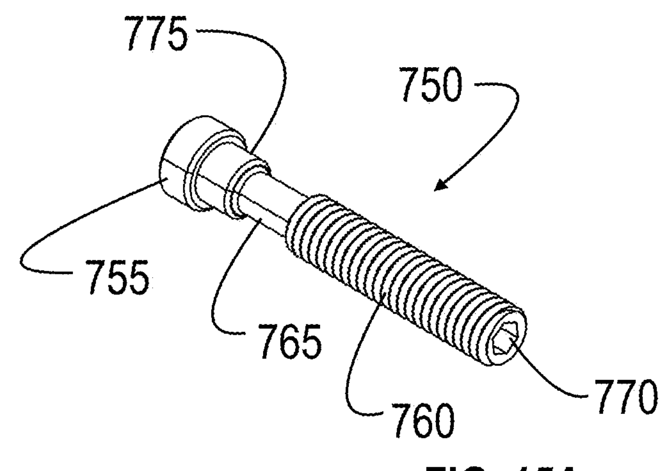
FIG. 15A is a perspective view of a height shaft of an expandable intervertebral implant according to an embodiment.
Figure 15B:
FIG. 15B is a front view of the height shaft of the expandable intervertebral implant FIG. 15A.
Figure 15C:
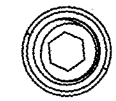
FIG. 15C is a side view of the height shaft of the expandable intervertebral implant FIG. 15A.

FIG. 15A is a perspective view of a height shaft 750 of an expandable intervertebral implant 1000 according to an embodiment. FIG. 15B is a front view of the height shaft 750 of the expandable intervertebral implant 1000 and FIG. 15C is a side view of the height shaft 750 of the expandable intervertebral implant 1000. The height shaft 750 may be configured to be part of an expansion mechanism. The pusher 600 may convert rotational motion of the height shaft 750 into linear motion of a height wedge bottom 300. The height shaft 750 may include a first diameter 755; a second diameter 775; and a third diameter 765. The first diameter 755 may be configured to rotatably engage a pocket 465 of an inferior plate 400.

The second diameter 775 may be configured to rotatably engage an opening 468 of an inferior plate 400. The first diameter 755 may be configured to be larger than the second diameter 775. Additionally, the first diameter 755 may be configured to be larger than the opening 468 so that the height shaft 750 is rotatably captive within the pocket 465. The second diameter 775 may be configured to be larger than the third diameter 765. The height shaft 750 may include a threaded portion 760 configured to engage a third threaded hole 620 of a pusher 600. The height shaft 750 may further include a first female drive feature 770 configured to facilitate rotation of the height shaft 750 through engagement with a drive tool. The first female drive feature 770 may be configured as a hex, a hexalobe, a square or other non-circular profile known in the art.

Figure 16A:
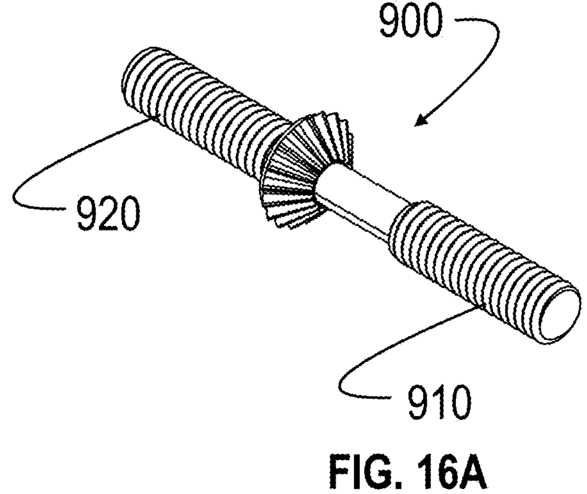
FIG. 16A is a perspective view of a turnbuckle of an expandable intervertebral implant according to an embodiment.
Figure 16B:
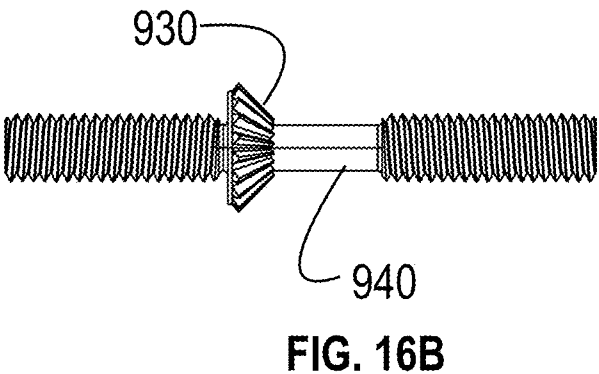
FIG. 16B is a front view of the turnbuckle of the expandable intervertebral implant of FIG. 16A.
Figure 16C:
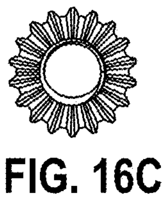
FIG. 16C is a side view of the turnbuckle of the expandable intervertebral implant of FIG. 16A.

FIG. 16A is a perspective view of a turnbuckle 900 of an expandable intervertebral implant 1000 according to an embodiment. FIG. 16B is a front view of the turnbuckle 900 of the expandable intervertebral implant 1000 and FIG. 16C is a side view of the turnbuckle 900 of the expandable intervertebral implant 1000. The turnbuckle 900 may include a first turnbuckle threaded portion 910; a second turnbuckle threaded portion 920; a second bevel gear face 930; and a turnbuckle shaft 940. The turnbuckle 900 may be configured to engage a bevel gear component 800 to transfer rotational motion along an axis of the bevel gear component 800 to rotational motion along an axis of the turnbuckle 900.

The first angle wedge 500 may include a first threaded hole 520 configured to threadably connect to a first turnbuckle threaded portion 910. The second angle wedge 550 may include a second threaded hole 570 configured to threadably connect to a second turnbuckle threaded portion 920. The first turnbuckle threaded portion 910 and the first threaded hole 520 may be configured with a left-handed thread and the second turnbuckle threaded portion 920 and the second threaded hole 570 may be configured with a right-handed thread. The first angle wedge 500, the second angle wedge 550, and the turnbuckle 900 may be configured so the rotation of the turnbuckle 900 results in translation of the first angle wedge 500 in a direction that is opposite to that of the second angle wedge 550.

The turnbuckle 900 and the bevel gear component 800 may make up a bevel gear mechanism configured to actuate movement of the first angle wedge 500 and/or the second angle wedge 550 in a medial-lateral direction. The bevel gear mechanism may include the turnbuckle, having a first axis of rotation, and the bevel gear, having a second axis of rotation. The first axis of rotation may be perpendicular to the second axis of rotation.

The expandable intervertebral implant 1000 may be manufactured from titanium alloy, titanium, stainless steel, cobalt chrome, PEEK, or other implant quality material with suitable mechanical properties. Additionally, or alternatively, one or more components of the expandable intervertebral implant 1000 may manufactured through additive manufacturing methods.

In some embodiments, one or more components of the expandable intervertebral implant 1000 may include a porous surface. The porous surface may be configured to promote bone in-growth. In some embodiments, the porous surface may be configured as a trabecular structure configured to promote bone in-growth. Additionally, or alternatively, the porous surface may be configured to include cells that are configured to receive biologic material prior to implantation to promote bone in-growth after implantation. Additionally, or alternatively, the porous surface may be configured to include less metal mass implanted and more open areas for the bone to grow through the implant and create a more rigid fusion of the superior vertebra and inferior vertebral body. In an embodiment, one or more components of the expandable intervertebral implant 1000 may be additively manufactured with integrated porous features configured for bone integration.

The expandable intervertebral implant 1000 may include flexible or compliant structures to perform or maintain expansion. The expandable intervertebral implant 1000 may include a single height wedge component comprising a living hinge in place of a height wedge top 200 configured to be rotatably coupled to a height wedge bottom and a height wedge pin 700.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

The phrases "generally parallel" and "generally perpendicular" refer to structures that are within 30° parallelism or perpendicularity relative to each other, respectively. Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the disclosure.

While specific embodiments and applications of the present disclosure have been illustrated and described, it is to be understood that the disclosure is not limited to the precise configuration and components disclosed herein. Various modifications, changes, and variations which will be apparent to those skilled in the art may be made in the arrangement, operation, and details of the methods and systems of the present disclosure without departing from its spirit and scope.

The invention claimed is:

1. An expandable intervertebral implant comprising:
a superior plate configured to engage a superior vertebra;
an inferior plate configured to engage an inferior vertebra, wherein the inferior plate is spaced apart from the superior plate by a gap;
one or more first sliders moveable along a first direction to urge linear expansion of the gap;
one or more second sliders moveable along a second direction, nonparallel to the first direction, to urge angular expansion of the gap; and
a bevel gear mechanism configured to actuate movement of the one or more second sliders along the second direction;
wherein:
the bevel gear mechanism comprises a turnbuckle comprising a first axis of rotation and a bevel gear comprising a second axis of rotation;
the first axis of rotation is perpendicular to the second axis of rotation; and
the turnbuckle is threadably connected to each of the one or more second sliders.

2. The expandable intervertebral implant of claim 1, wherein the first direction is generally anterior-posterior and the second direction is generally medial-lateral.

3. The expandable intervertebral implant of claim 1, wherein the one or more second sliders comprise:
a first second slider configured to move along the second direction; and
a second second slider configured to move along a direction opposite the second direction.

4. The expandable intervertebral implant of claim 1, wherein the one or more second sliders only indirectly contact the superior plate or the inferior plate.

5. The expandable intervertebral implant of claim 1, wherein each of the one or more first sliders is configured to urge linear expansion of the gap through movement in a single direction.

6. The expandable intervertebral implant of claim 1, wherein each of the one or more second sliders is moveable transverse to an anterior-posterior direction to urge expansion of the gap.

7. The expandable intervertebral implant of claim 1, wherein the one or more first sliders are moveable independently of motion of the one or more second sliders such that the linear expansion of the gap is independent of the angular expansion of the gap.

8. The expandable intervertebral implant of claim 1, wherein actuation of the linear expansion of the gap occurs before or after actuation of the angular expansion of the gap.

9. An expandable intervertebral implant comprising:
a superior plate configured to engage a superior vertebra;
an inferior plate configured to engage an inferior vertebra, wherein the inferior plate is spaced apart from the superior plate by a gap;
a first slider moveable transverse to an anterior-posterior direction to urge expansion of the gap;
a second slider moveable in a direction opposite to the first slider to urge expansion of the gap; and
a bevel gear mechanism configured to actuate movement of the first slider;
wherein:
the bevel gear mechanism comprises a turnbuckle comprising a first axis of rotation and a bevel gear comprising a second axis of rotation;
the first axis of rotation is perpendicular to the second axis of rotation; and
the turnbuckle is threadably connected to the first slider and the second slider.

10. The expandable intervertebral implant of claim 9, wherein the first slider only indirectly contacts the superior plate or the inferior plate.

11. An expandable intervertebral implant comprising:
a superior plate configured to engage a superior vertebra;
an inferior plate configured to engage an inferior vertebra, wherein the inferior plate is spaced apart from the superior plate by a gap;
a bevel gear mechanism; and
an expansion mechanism, configured to urge linear expansion and angular expansion of the gap, comprising a height wedge top coupled with the superior plate and a height wedge bottom coupled with the inferior plate,
wherein:
the height wedge top is configured to remain parallel to the superior plate during linear expansion and angular expansion of the gap;
the height wedge bottom is configured to remain parallel to the inferior plate during linear expansion and angular expansion of the gap;
the expansion mechanism further comprises one or more first sliders moveable along a first direction to urge linear expansion of the gap;
the expansion mechanism further comprises one or more second sliders moveable along a second direction, nonparallel to the first direction, to urge angular expansion of the gap;
the bevel gear mechanism is configured to actuate movement of the one or more second sliders along a second direction and comprises a turnbuckle comprising a first axis of rotation and a bevel gear comprising a second axis of rotation;
the first axis of rotation is perpendicular to the second axis of rotation; and
the turnbuckle is threadably connected to each of the one or more second sliders.

12. The expandable intervertebral implant of claim 11, wherein the height wedge top is rotatably coupled to the height wedge bottom.

13. The expandable intervertebral implant of claim 11, wherein the height wedge top is translatable with respect to the superior plate in an inferior-superior direction and an anterior-posterior direction.

14. The expandable intervertebral implant of claim 11, wherein the one or more second sliders only indirectly contact the superior plate or the inferior plate.

15. The expandable intervertebral implant of claim 11, wherein the one or more first sliders are movable independently of motion of the one or more second sliders such that the linear expansion of the gap is independent of the angular expansion of the gap.

* * * * *